United States Patent [19]
Kelley

[11] Patent Number: 5,827,238
[45] Date of Patent: Oct. 27, 1998

[54] ROLLER CLAMP-CONNECTOR ASSEMBLY

[75] Inventor: Richard Kelley, Tyngsboro, Mass.

[73] Assignee: Microwave Medical Systems, Inc., Acton, Mass.

[21] Appl. No.: 961,356

[22] Filed: Oct. 30, 1997

[51] Int. Cl.⁶ ....................................... A61M 5/00
[52] U.S. Cl. ................ 604/250; 285/314; 604/283; 604/905
[58] Field of Search .............. 604/250, 29, 905, 604/283; 285/314, 315, 320

[56] References Cited

U.S. PATENT DOCUMENTS 4,614,514  9/1986  Carr et al. ................ 604/113
4,889,527  12/1989  Herrli ........................ 604/29

Primary Examiner—Wynn Wood Coggins
Assistant Examiner—N. Kent Gring
Attorney, Agent, or Firm—Cesari and McKenna, LLP

[57] ABSTRACT

A connector/clamp assembly for a transfer set includes an inlet connector with a base, a shank extending from one end of the base and an I.V. tube extending from the opposite end of the base. The base interfits with a housing having opposite ends, a bottom wall and a pair of side walls extending from the bottom wall, so that the shank extends from one end of the housing and the tube extends along the bottom wall to the opposite end of the housing. A clamp is present in the housing opposite the tube and which is movable within the housing between a first position wherein the clamp collapses the tube against the housing bottom wall thereby blocking the tube lumen and a second position wherein the clamp does not collapse the tube sufficiently to appreciably occlude the lumen.

11 Claims, 2 Drawing Sheets

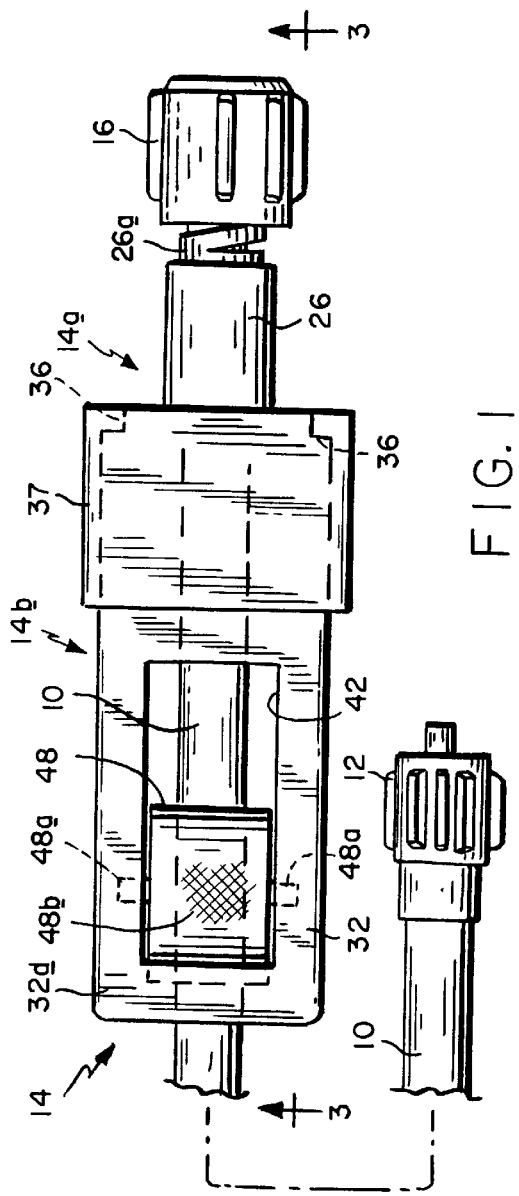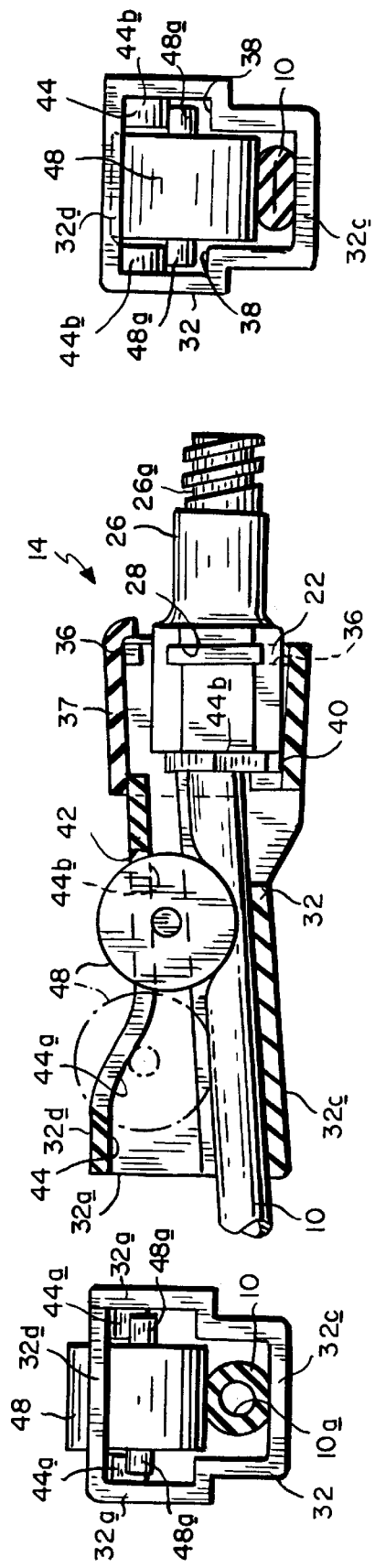

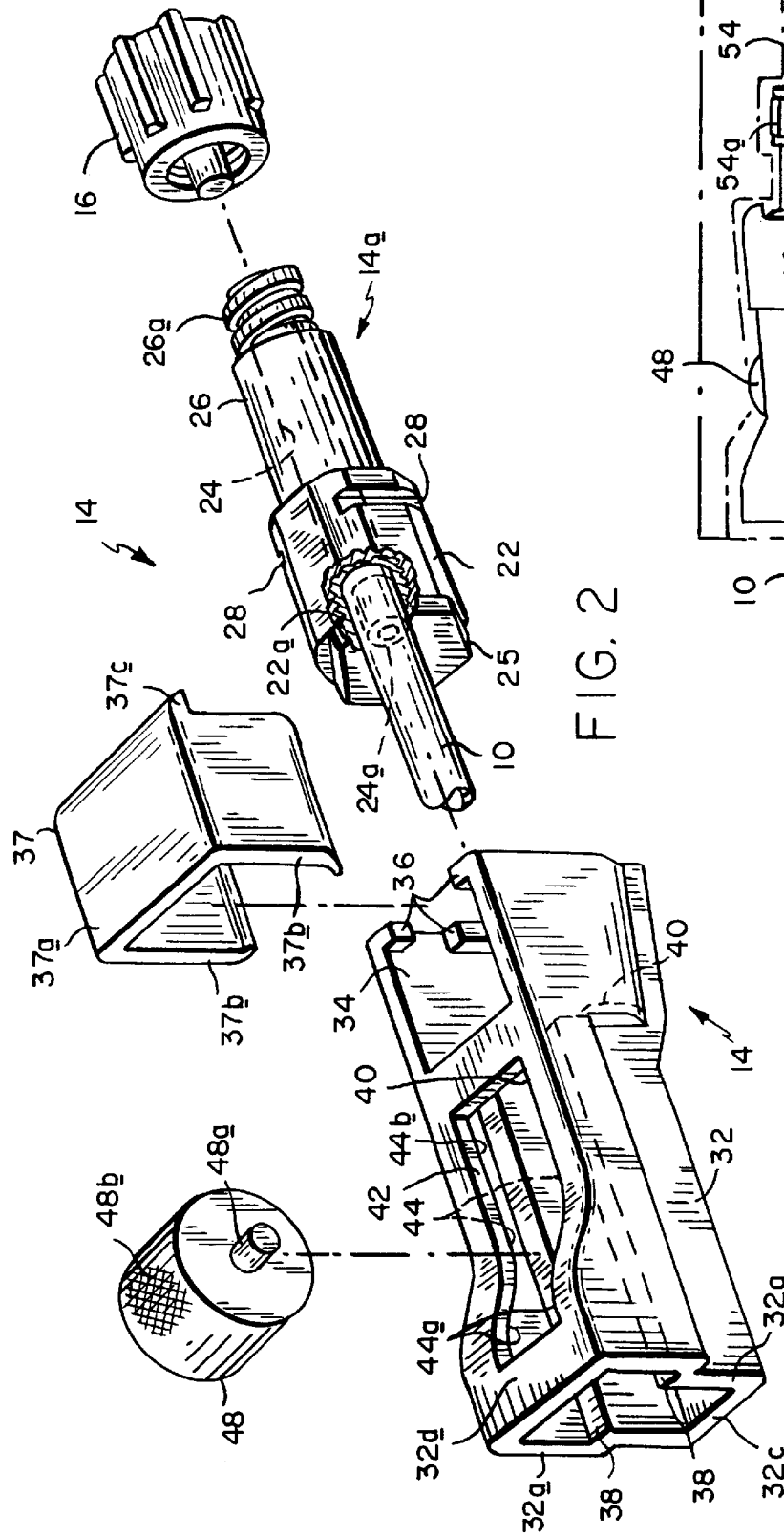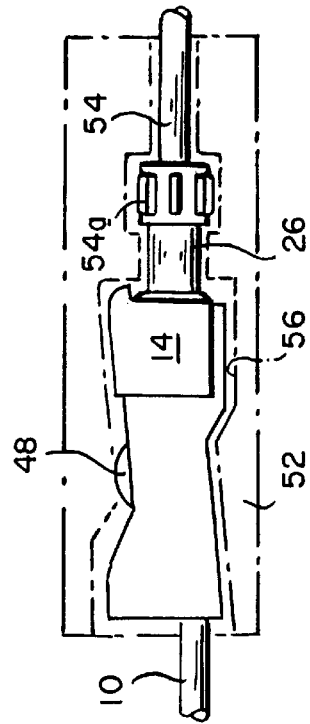

ROLLER CLAMP-CONNECTOR ASSEMBLY

This invention relates to a roller clamp-connector assembly. It relates especially to an assembly of this type incorporated into a transfer set.

BACKGROUND OF THE INVENTION

Patients undergoing dialysis are fitted with an infusion set including a catheter leading to the peritoneum and which has to be coupled periodically to a dialysis solution bag. Usually, the connection is made by way of a peritoneal dialysis (PD) transfer set which basically consists of a tube about two feet long, having connectors at its opposite ends and a clamp for clamping the tube. The outlet connector at the distal end of the tube is coupled to a mating connector on the infusion set; the inlet connector at the proximal end of the tube is coupled to the connector of an I.V. line leading to the dialysis solution bag or infusion system.

The basic function of the transfer set is to provide slack in the I.V. line leading from the dialysis solution bag or infusion system to the patient and to allow blocking of the I.V. line when the transfer set is disconnected from the solution bag or infusion system. Since a transfer set may remain connected to the patient for 6-months or longer, the connector at the proximal or inlet end of the transfer set may be connected and disconnected from the dialysis solution bag or infusion system several times per day, normally four times. In many cases, these connections are made by the patients themselves during continuous ambulatory peritoneal dialysis (CAPD).

Also, as part of the procedure, the transfer set connector is flushed out periodically to remove any contamination or other debris that may tend to occlude the transfer set connector. This involves connecting the inlet connector at the proximal end of the transfer set to a bag set consisting of an elevated bag containing flushing liquid (e.g., dialysate solution) and a waste bag, both being connected by way of a Y-connector to the inlet connector of the transfer set. The I.V. lines from the two bags are provided with clamps.

During the procedure, first, the patient drains the used or old dialysate fluid from his/her person into the waste bag. This is done by lowering or placing the waste bag on the floor. To perform the drain procedure, the clamps on the drain line and the transfer set are opened. After draining, the clamp on the transfer set is closed. The new solution is elevated to a position above the patient's infusion site. The supply line (i.e., the new fluid) is then opened to allow flushing of the transfer set connector using a small amount of the new dialysis solution. The drain line clamp is then closed and the clamp on the transfer set is opened, allowing the new dialysate solution to be transferred into the patient. Once the fluid is transferred, all clamps are placed in the "closed" position. Following each transfer, the "Y-set" (including waste bag and the new bag) are disposed of in an approved manner. The connector on the patient transfer set is normally terminated with a protective cap. The transfer set is then rolled up and secured to the patient's body. This sequence is repeated several times during the day, customarily four times, allowing four hours between exchanges.

It is apparent from the foregoing that many connections to the transfer set's inlet connector have to be made over time. Presently, hospital personnel and patients are instructed to be very careful about making sure that such connections are made without directly contacting the connectors that are being coupled together. This is obviously a problem particularly for the elderly and those that lack the manual dexterity and good eyesight that is required to make the connections between the transfer set and the dialysis machine or source of flushing liquid. Accordingly, bacteria, such as staphylococcus bacteria, may tend to collect at the inlet connector of the transfer set.

It is obvious, then, that unless steps are taken to prevent it, the bacteria present in the connector may be entrained in the fluid flowing through the transfer set and be carried into the patient where it could cause a serious infection.

Relatively recently, a procedure has been developed whereby a microwave sterilizer apparatus couples the inlet connector of the transfer set to the fluid source while clamping the I.V. line on opposite sides of the connector so as to isolate a small volume of liquid within the connector. Following clamping, the sterilizer apparatus heats the trapped liquid in the connector to a high enough temperature, e.g., over 100° C., for a sufficient length of time, e.g., 30 sec. or less, to disinfect or sterilize the surfaces of the connector components in contact with the fluid. Therefore, when the I.V. lines on opposite sides of the connector are unclamped, the fluid conducted to the patient is essentially free of bacteria. Apparatus such as this is disclosed in U.S. Pat. No. 4,614,514, the contents of which is hereby incorporated by reference herein.

For the disinfection technique described in the above patent to be effective, however, it is desirable that the fluid line between the transfer set's connector and clamp be as short as possible. Only in this way can the parts be disinfected completely and in a reasonably short time. In other words, the larger the volume of liquid that has to be heated, the longer it takes to complete the disinfection or sterilization process.

While various different types of transfer sets are in existence, none of them are suitable for disinfection or sterilization by a microwave sterilizer as described above. More particularly, some transfer sets have a relatively large roller clamp spaced along the I.V. tube from the set's inlet connector. This makes it difficult to adequately heat the liquid between the inlet connector and the clamp during the disinfection or sterilization process. Therefore, some bacteria may still remain in the upstream end of the transfer set and be carried into the patient during the next infusion.

We are also aware of a transfer set fitted with an integral inlet connector/clamp assembly which incorporates a cam. When opposite ends of the assembly are rotated relatively, the cam clamps the tube. However, that assembly is still quite long so that there is an appreciable tubing length between the connecting and clamping portions of that assembly. Therefore, it is impractical to disinfect that transfer set by a microwave sterilization process. Also, two hands are required to operate the clamp in that assembly, one to hold one end of the assembly stationary and the other to rotate the clamping end of the assembly. Therefore, it is difficult for CAPD patients, particularly elderly or infirm patients to use that transfer set in an approved manner.

SUMMARY OF THE INVENTION

The present invention aims to provide a PD transfer set with an integral connector/clamp assembly which is especially suitable for microwave disinfection or sterilization.

Another object of the invention is to provide a PD transfer set connector/clamp assembly having a minimum length so as to minimize the tubing length between the connector and clamping portions of the assembly.

A further object of the invention is to provide an assembly of this type which is easy to operate using only one hand.

Another object of the invention is to provide such a connector/clamp assembly which is composed of only a few relatively inexpensive, molded parts which are easy to make and to assemble.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

Generally, the connector/clamp assembly of the invention comprises an inlet connector for connection to one end of a length of I.V. tubing whose other end is terminated by a standard mating connector. Both connectors may be more or less standard screw-type connectors of the type commonly used on transfer sets. However, the present inlet connector is modified to include a pair of slots on opposite sides of the connector base to enable the incorporation of the connector into the housing of a specially designed roller clamp.

That housing is formed as a box girder having a forward segment adapted to interlockingly receive the connector base and a rear segment for accommodating the tubing leading from the connector which tubing extends out through the distal end of the housing. Positioned in the rear end segment of the housing is a roller which is movable along the housing on a track constituted by rails formed in the interior side walls of the housing. The track is shaped so that when the roller is positioned adjacent to the distal end of the housing, the roller is spaced from the bottom wall of the housing by a distance that provides clearance for the tubing extending along the housing. On the other hand, when the roller is moved to a proximal position along the housing, the track urges the roller relatively close to the bottom wall of the housing so that a segment of tubing is clamped between the roller and the bottom wall of the housing thereby blocking fluid flow through the tubing.

It is a feature of the invention that the roller component of the assembly can be moved between its clamping and unclamping positions using only one hand. Furthermore, the transition between the clamping and unclamping positions is readily apparent to the user because of the great difference in back pressure on the user's thumb due to the tubing. Therefore, the device is quite easy to operate even by aged or infirm individuals who have to make repeated connections to the transfer set of which the assembly is a part.

Due to its unique construction, the subject connection/clamp assembly is quite short. Therefore, there is minimum tubing volume between the connecting and clamping portions of the assembly. While prior comparable assemblies may have a fluid column in the assembly of 5 cc, the present assembly defines a column only 0.4 cc long. This enables the present assembly to be positioned in its entirety in a microwave sterilizer so that the entire assembly including the tubing component therein can be disinfected or sterilized in a minimum amount of time.

With all of the above advantages, the subject connector/clamp assembly is still relatively easy and inexpensive to make. It is composed of only four molded plastic parts, one of which is a standard Luer connector modified to include slots. These parts can be made quite inexpensively in quantity. Furthermore, the parts are easy to assemble. Therefore, the assembly should be quite competitive with those already in use which do not have the aforesaid advantages.

BRIEF DESCRIPTION OF THEE DRAWINGS

For a fuller understanding of the nature and objects of the invention reference should be made to the following detailed description taken in connection with the accompanying drawings, in which:

FIG. 1 is a top plan view, with parts broken away, showing a transfer set incorporating a connector-clamp assembly according to the invention;

FIG. 2 is an exploded perspective view showing the components of the FIG. 1 assembly in greater detail;

FIG. 3 is a sectional view taken along line 3—3 of FIG. 1;

FIGS. 4A and 4B are end views showing the FIG. 1 assembly in its unclamping and clamping conditions, respectively, and FIG. 5 is a diagrammatic view of the FIG. 1 connector-clamp assembly being sterilized in a microwave sterilizer.

DETAILED DESCRIPTION OF AN ILLUSTRATIVE EMBODIMENT

Refer now to FIG. 1 of the drawings which shows a PD transfer set comprising a resilient I.V. tube 10, which is usually about two feet long, having a conventional screw-type male connector 12 secured to its distal end. Connected to the opposite or proximal end of tube 10 is applicant's novel connector-clamp assembly shown generally at 14. Assembly 14 includes a tubular connector section shown generally at 14a and a clamp section indicated generally at 14b. These two sections are interconnected end-to-end to form a unit having a relatively small overall length, i.e., in the order of 2.5 inches.

When the transfer set is in use, the connector section 14a is connected to a mating connector at the end of an I.V. line leading from a fluid source such as a bag set or a dialysis machine, while the connector 12 at the distal end of the transfer set is coupled to the mating connector of an infusion set implanted in a patient. Fluid flow through the transfer set is controlled by manipulating the assembly's clamp section 14b as will be described.

When the transfer set is not in use, the end of section 14a may be closed by a protective cap 16.

Preferably, all of the components of the assembly 14 are made of medical grade plastic materials which can withstand most heat sterilization as well as Ethylene Oxide (ETO) and/or gamma sterilization.

Referring now to FIGS. 1 to 3, the tubular connector section 14a comprises a 4-sided base 22. The proximal end of tube 10 extends into the distal end of base 22 and is secured thereto such that the tube is in fluid communication with an axial passage 24 (FIG. 2) in section 14a. which passage extends the entire length of that section. More particularly, as best seen in FIG. 2, the base 22 has a threaded axial recess 22a at its distal end containing an axial tubular nipple 24a which leads to passage 24. The proximal end of tube 10 is slid onto nipple 24a and mechanically secured by a threaded bushing 25 screwed into recess 22a which jams or compresses the tubing 10 wall against the nipple thereby achieving a fluid tight seal. Preferably, the connector section 14a is molded from a rugged high temperature plastic material which allows repeated use of the connector section 14a on the patient set.

Extending from the opposite or proximal end of base 22 is a reduced diameter shank 26 terminated by a threaded segment 26a which is substantially identical to a screw-type female Luer connector customarily used in the medical field. A pair of slots 28 are present at opposite sides of base 22 near the forward end thereof. These slots are directly opposite one another and extend perpendicular to the longitudinal axis of section 14a.

The clamp section 14b of assembly 14 comprises an elongated hollow housing 32 formed as a box girder having a T-shaped crossection as seen in FIG. 4A. More particularly, the housing includes a pair of mirror-image side walls 32a, 32a connected by a bottom wall 32c and a top wall 32d. A generally rectangular opening 34 is provided in the top wall 34d which extends to the proximal end of the housing. Also, a pair of mirror-image flanges 36 are present at the proximal end of the housing. These flanges extend perpendicular to the housing longitudinal axis and are adapted to be received in the slots 28 in assembly section 14a as will be described later.

The assembly 14 also includes an inverted U-shaped bracket 37 which is designed to retain section 14a in section 14b as will be described later. Suffice it to say now that bracket 37 includes a top wall 37a, a pair of mirror-image side walls 37b which extend down from wall 37a and a brow 37c that projects forwardly from top wall 37a.

The segments of housing side walls 32a to the rear of opening 34 are stepped to form shoulders which define a pair of horizontal internal ledges 38. These ledges extend from the distal end of housing 32 to points almost directly below the closed end of opening 34 in top wall 32d. At the points where the ledges terminate under opening 34, the housing side walls 32a are shaped to define a pair of internal mirror-image vertical stops 40 at opposite sides of the housing; see FIGS. 2 and 3. These stops cooperate with the flanges 36 to capture the assembly section 14a when that section is installed in housing 32 as will be described later.

A generally rectangular opening 42 is provided in the housing top wall 32b between opening 34 and the distal end of the housing. Also, at the distal end of the housing, the housing side walls 32a are higher than they are midway along the housing. Accordingly, at the distal end of opening 42, the top wall 32d is spaced farther away from bottom wall 32c than it is adjacent to the opposite end of opening 42. Resultantly, the undersides of the opposite side edges of opening 42 form a track constituted by a pair of mirror-image parallel rails or flanges 44. These rails have first segments 44a adjacent to the distal end of housing 32 which are parallel to and spaced a fixed distance above ledges 38 and second segments 44b which are still parallel to ledges 38 but are spaced a lesser distance above those ledges. Still further, and as best seen in FIG. 3, the bottom wall 32c of housing 32 is sloped so that at the distal end of the housing, the bottom wall is spaced further below ledges 38 than it is midway along the housing.

As shown in FIGS. 1 to 3, the clamp section 14b of assembly 14 also includes a cylindrical roller 48 having a pair of collinear shafts 48a extending from opposite sides of the roller. Preferably, the cylindrical surface 48b of roller 48 is knurled or otherwise roughened to form a good finger gripping surface.

Roller 48 is designed and dimensioned to fit in housing 32 so that a relatively large sector of its cylindrical surface 48b projects through opening 42 in housing top wall 32d and so that its shafts 48a engage under and roll along the rails 44 at the opposite sides of that opening.

To assemble assembly section 14a to section 14b, the I.V. tube 10 having its proximal end attached to connector base 22 is threaded through housing 32 from the proximal end thereof. Then, the base 22 of assembly section 14a is inserted into the proximal end of housing 32 through the top opening 34 therein so that the flanges 36 at the proximal end of the housing slide into the slots 28 in base 22 and so that the connector shank 26 projects from the proximal end of the housing. When properly seated, base 22 is captured between flanges 36 and the stops 40 formed in the housing side walls. Section 14a may then be permanently coupled to the housing by engaging the bracket 37 onto the proximal end segment of the housing 32 so that the bracket completely covers opening 34 therein as shown in FIGS. 1 and 2. The bracket may be permanently secured to the housing by a solvent bond or the like.

Then, the roller 48 is forced into the distal end of the housing 32 in opposition to the bias presented by the resilient I.V. tube 10. The roller snaps into opening 42 as shown in FIGS. 1 and 3 so that its shafts 48a engage under rails 44.

Roller 48 can roll along rails 44 between an unclamping position shown in dashed lines in FIG. 3 to a clamping position shown in solid lines in that figure. When the roller is in its unclamping position adjacent to the distal end of opening 42, its circumferential surface 48a is spaced from the housing bottom wall 32c by rail segments 44a a distance more or less equal to the outer diameter of tube 10. Therefore, substantially no compression force is exerted on the tube. Accordingly, its lumen 10a has a normal crossection and fluid flow therethrough is not impeded as seen from FIG. 4A However, when roller 48 is moved to its clamping position adjacent to the proximal end of opening 42, it is urged by the rail segments 44b closer to bottom wall 32c in opposition to the force exerted by the resilient tube 10 so that the tube is collapsed between the cylindrical surface 48b of the roller and the housing bottom wall 32c with result that the tube lumen 10a is completely closed as seen in FIG. 4B. Accordingly, all fluid flow through tube 10 to the roller is stopped.

It is a feature of the invention that the roller 48 may be rolled easily between its clamping and unclamping positions by thumb pressure on the roller while holding the assembly 14 with one hand. Furthermore, the relatively sharp or steep transition between rail segments 44a and 44b makes it readily apparent to the user when the roller is in its two positions. Resultantly, the clamping section 14b operates more or less as a binary or on/off valve rather than, as in some prior assemblies of this general type, as a variable flow regulator wherein the distinction between the flow and no flow conditions is less apparent.

Refer now to FIG. 5 which illustrates assembly 14 being disinfected or sterilized in a microwave disinfection apparatus or sterilizer 52 shown in phantom in that figure. The apparatus 52 may be of a clam shell type disclosed in the above patent. With clamping section 14b in its clamped condition, the upstream segment of tube 10 may be filled with solution and shank 26 coupled to the standard connector 54a of I.V. tubing 54 leading from a solution bag or dialysis system (not shown). Resultantly, a small volume of fluid is trapped at the transfer set-to-solution bag connection. Assembly 14 may then be positioned in the heating cavity 56 of device 52.

When the disinfection or sterilization apparatus is activated, the microwave energy produced in cavity 56 heats the solution trapped between the clamped portions of the tube 10 and the solution bag connector break away seal to a temperature high enough to disinfect or sterilize all of the internal surfaces of assembly 14 (including tube 10) within the cavity. Because the volume of the trapped solution is relatively small, it can be brought to a suitable temperature in a minimum amount of time. Typically an 85° C. (s.d.=2.4° C., n=10) rise in solution temperature may be seen in about 12 seconds, thus yielding temperatures well over 100° C. with a starting temperature of 25° C.

Integrating the clamp and connector in assembly 14 eliminates the length of tubing adjacent to the connector normally present in the cavity which tubing could change dimensions under increased temperature and pressure and adversely affect the operation of the apparatus.

Furthermore, since the clamp section 14b of assembly 14 is contained within the heating cavity 56, the interior of tube 10 all the way down to the pinched segment of the tube underlying roller 48 is disinfected or sterilized. Therefore, there are no bacteria in the tube that could be delivered to the patient after the assembly is removed from the apparatus device and flow through tube 10 is resumed by moving roller 48 to its unclamping position.

The design of apparatus 52 is improved over the apparatus disclosed in the above patent in that microwave heating cavity 54 is profiled to accumulate the connector-clamp assembly 14. The assembly thus eliminates the need for the apparatus to include means for pinching the tubing to maintain a pressure seal, thus greatly simplifying the cavity design and closure action while at the same time reducing the cost of the apparatus 52.

The improved design also ensures a fixed or constant volume of fluid in the cavity so that a high degree of disinfection of all fluid beyond the clamping section 14b is assured.

Still further, the fact that the cavity 54 is profiled to position assembly 14 centrally in the cavity greatly improves heating efficiency and reduces the cycle time of apparatus 52.

In this connection, it should be understood that the position of the fluid within the cavity is very important to the efficiency of the device. A proper amount of fluid is required to provide a sufficient microwave absorber to achieve wider cavity bandwidth to accommodate both the transfer set connector/clamp assembly when mated to either the mating dialysis system or bag connector, or the terminating cap 16.

When the apparatus 52 is in operation, the total fluid contained with the connector assembly 14 is now elevated in temperature. This high temperature results in a sufficiently high reflection in cavity 54 to effectively reduce the applied power thereby limiting further elevation of temperature and pressure within assembly 14. In other words, the overall system is self-limiting with regard to temperature.

Preferably, apparatus 52 operates at a frequency of 2450 MHz instead of the patented apparatus '915 MHz to eliminate the need for dielectric loading of cavity 54. The air-filled cavity 54 at 2450 MHz results in the same physical size as the dielectric-filled cavity at 915 MHz. The elimination of the dielectric significantly reduces the overall weight of apparatus 52.

In one working example, connector pairs were prepared for testing by sealing the transfer set connector 14a with its integral clamp 14b and filing this connector with dialysate solution and a suspension containing at least $10^6$ colony forming units (CFU) of a test microorganism. The filled transfer set connector was then mated with a sterile CAPD bag connector 54a. Approximately 0.4 ml of solution was contained within the mated connector pair. Using standard D-value determination methods, data were obtained for surviving organisms versus six exposure times to obtain a population reduction curve. Four microorganisms (*S. epidermidis, P. aeruginosa, C. albicans* and *A. niger*) recognized to be among the most prevalent or problematic in causing peritonitis were tested. After microwave heating in cavity 56, the treated solution was aseptically withdrawn from the connector pair using a needle and syringe, plated in growth media and incubated. Population counts of CFUs after incubation were used to establish survival curves. Organisms were tested individually in three trials at each of six exposure times. Results showed a population reduction of greater than 6 log in less than 18 seconds (D-value<3 seconds) for all organisms tested. One potential benefit of using this new method is the destruction of the gram-negative bacteria and fungal organisms that have been difficult to flush or to destroy with other CAPD exchange methods.

As noted above, all of the components of assembly 14 are simple molded plastic parts which are easy to manufacture in quantity. Also, as seen from the foregoing, the components of the assembly are easy to assemble. Therefore, a transfer set incorporating the assembly 14 can be manufactured at minimum cost so it can be used as a disposable item whenever PD dialysis procedures are being performed.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawings, shall be interpreted as illustrative and not in a limiting sense.

It is also to be understood that the following claims are intended to cover all of the generic and specific features of the invention described herein.

What is claimed is:

1. A connector/clamp assembly for a transfer set, said assembly comprising a tubular inlet connector having a base and a shank extending from the base;

an I.V. tube having one end connected to the base, an opposite end and a lumen extending between said ends;

a housing having opposite ends, a bottom wall and a pair of side walls extending from the bottom wall, said base interfitting with said housing so that said shank extends from one end of the housing and the tube extends along the bottom wall to the opposite end of the housing, and clamping means in the housing opposite the tube, said clamping means being movable within the housing between a first position wherein the clamping means collapses the tube against the housing bottom wall thereby blocking said lumen and a second position wherein the clamping means does not collapse the tube sufficiently to appreciably occlude the lumen said clamping means including means defining a track extending along the housing, and a roller positioned in the housing for rolling along the track, said track having a first segment which spaces the roller from the housing bottom wall a distance no less than the diameter of the tube and a second segment which spaces the roller from said bottom wall a much lesser distance sufficient to collapse the tube and block the lumen.

2. The assembly defined in claim 1 wherein the track includes a relatively sharp transition between the first and second track segments.

3. The assembly defined in claim 1 wherein the roller includes a pair of collinear shafts projecting from opposite sides of the roller, and the track is constituted by a pair of mirror-image rails or flanges in the housing side walls which overlie said shafts.

4. The assembly defined in claim 1, wherein the inlet connector is a threaded connector, and further including a mating threaded outlet connector secured to the other end of the tube.

5. The assembly defined in claim 4 wherein the inlet and outlet connectors are female and male threaded connectors, respectively.

6. The assembly defined in claim 1 and further including a housing top wall extending between the housing side walls;

a first opening in the top wall adjacent to said one end of the housing for receiving the connector base, and a bracket secured to the housing and covering said first opening.

7. The assembly defined in claim 6 wherein said base is formed with slots, and said housing side walls have mirror image flanges at said one end of the housing, said flanges being received in said slots to prevent relative motion of the connector and housing.

8. The assembly defined in claim 6 and further including a second opening in the housing top wall through which at least a portion of said roller projects.

9. The assembly defined in claim 1 and further including a volume of liquid in said tube segment upstream from said clamping means when the clamping means is in said second position;

means for releasably connecting said shank fluidically to a solution bag;

heating means for producing electromagnetic energy in a heating cavity, and means for positioning said connector, housing tube segment and clamping means in said heating cavity so that said heating cavity surrounds said connector, housing tube segment and clamping means whereby said energy heats said liquid to a temperature high enough to disinfect or sterilize all of the assembly surfaces exposed to said liquid.

10. A connector/assembly for a transfer set, said assembly comprising a tubular inlet connector having a base and a shank extending from the base;

an I.V. tube having one end connected to the base, an opposite end and a lumen extending between said ends;

a housing having opposite ends, a bottom wall and a pair of side walls extending from the bottom wall, said base intermitting with said housing so that said shank extends from one end of the housing and the tube extends along the bottom wall to the opposite end of the housing;

a finger-actuated roller clamp mounted in the housing opposite the tube, said clamp being movable within the housing between a first position wherein the clamp collapses the tube thereby blocking said lumen and a second position wherein the clamp does not collapse the tube sufficiently to appreciably occlude the lumen, and means for releasably maintaining the clamp in said first and second positions.

11. The connector/clamp assembly defined in claim 10 and further including a volume of liquid in said tube segment upstream from said clamp when the clamp is in said second position;

means for releasably connecting said shank fluidically to a solution bag;

heating means for producing electromagnetic energy in a heating cavity, and means for positioning said connector, housing tube segment and clamp in said heating cavity so that said heating cavity surrounds said connector, housing tube segment and clamp whereby said energy heats said liquid to a temperature high enough to disinfect or sterilize all of the assembly surfaces exposed to said liquid.

* * * * *